(12) United States Patent
Albertorio et al.

(10) Patent No.: US 8,439,976 B2
(45) Date of Patent: May 14, 2013

(54) INTEGRATED ADJUSTABLE BUTTON-SUTURE-GRAFT CONSTRUCT WITH TWO FIXATION DEVICES

(75) Inventors: Ricardo Albertorio, Naples, FL (US); Craig D. Morgan, Greenville, DE (US); Jacob A. Jolly, Naples, FL (US); Eric S. Zajac, Naples, FL (US)

(73) Assignee: Arthrex, Inc., Naples, FL (US)

( * ) Notice: Subject to any disclaimer, the term of this patent is extended or adjusted under 35 U.S.C. 154(b) by 229 days.

(21) Appl. No.: 12/751,897

(22) Filed: Mar. 31, 2010

(65) Prior Publication Data

US 2010/0256677 A1    Oct. 7, 2010

Related U.S. Application Data

(60) Provisional application No. 61/165,343, filed on Mar. 31, 2009, provisional application No. 61/259,507, filed on Nov. 9, 2009, provisional application No. 61/311,234, filed on Mar. 5, 2010, provisional application No. 61/311,211, filed on Mar. 5, 2010.

(51) Int. Cl.
*A61F 2/08* (2006.01)

(52) U.S. Cl.
USPC ..................................................... 623/13.14

(58) Field of Classification Search ...... 623/13.11–13.2; 606/232, 148, 151, 139, 144, 228
See application file for complete search history.

(56) References Cited

U.S. PATENT DOCUMENTS

| | | | | | |
|---|---|---|---|---|---|
| 3,176,316 A | * | 4/1965 | Bodell | ......................... | 623/13.19 |
| 4,301,551 A | * | 11/1981 | Dore et al. | ................ | 623/13.13 |
| 4,400,833 A | * | 8/1983 | Kurland | ..................... | 623/13.17 |
| 4,776,851 A | * | 10/1988 | Bruchman et al. | ......... | 623/13.11 |
| 4,790,850 A | * | 12/1988 | Dunn et al. | ................. | 623/13.19 |
| 4,792,336 A | * | 12/1988 | Hlavacek et al. | .......... | 623/13.18 |
| 4,851,005 A | * | 7/1989 | Hunt et al. | .................. | 623/13.11 |
| 4,863,471 A | * | 9/1989 | Mansat | ........................ | 623/13.2 |
| 4,917,700 A | * | 4/1990 | Aikins | ........................ | 623/13.19 |
| 4,932,972 A | * | 6/1990 | Dunn et al. | ................. | 623/13.19 |
| 5,024,669 A | * | 6/1991 | Peterson et al. | ............ | 623/13.14 |
| 5,026,398 A | * | 6/1991 | May et al. | ................... | 623/13.11 |
| 5,129,902 A | * | 7/1992 | Goble et al. | ..................... | 606/65 |
| 5,171,274 A | * | 12/1992 | Fluckiger et al. | .......... | 623/13.16 |
| 5,211,647 A | | 5/1993 | Schmieding | | |
| 5,217,495 A | * | 6/1993 | Kaplan et al. | .............. | 623/13.18 |
| 5,263,984 A | * | 11/1993 | Li et al. | ...................... | 623/13.18 |
| 5,266,075 A | * | 11/1993 | Clark et al. | ................... | 606/138 |
| 5,306,301 A | * | 4/1994 | Graf et al. | ..................... | 606/232 |
| 5,320,626 A | | 6/1994 | Schmieding | | |
| 5,397,357 A | * | 3/1995 | Schmieding et al. | ........ | 606/86 R |
| 5,562,669 A | * | 10/1996 | McGuire | .................... | 623/13.12 |

(Continued)

*Primary Examiner* — Alvin J. Stewart
(74) *Attorney, Agent, or Firm* — Dickstein Shapiro LLP

(57) ABSTRACT

An adjustable button/loop device for securing biologic material in bone, such as for ACL reconstruction. The device has a pair of button/loop constructs, each including a flexible, adjustable loop integrated with a fixation device (for example, a wedge). Biologic material (for example, soft tissue, graft, ligament or tendon) is secured to the two fixation devices, and the construct is inserted into a pair of bone sockets/tunnels, such as into a tunnel in the tibia and a socket in the femur. The biologic material is secured within the bone by passing the buttons though respective bone sockets/tunnels, flipping and seating the buttons outside the bone, and then adjusting the lengths of the flexible adjustable loops passing through the buttons and the respective fixation devices, with the graft extending between the fixation devices thereby appropriately secured in the bone.

4 Claims, 15 Drawing Sheets

U.S. PATENT DOCUMENTS

| | | | |
|---|---|---|---|
| 5,575,819 A * | 11/1996 | Amis | 623/13.13 |
| 5,628,756 A * | 5/1997 | Barker et al. | 606/139 |
| 5,643,266 A * | 7/1997 | Li | 623/13.13 |
| 5,645,588 A * | 7/1997 | Graf et al. | 606/151 |
| 5,931,869 A * | 8/1999 | Boucher et al. | 128/898 |
| 5,961,520 A * | 10/1999 | Beck et al. | 606/232 |
| 6,056,752 A * | 5/2000 | Roger | 623/13.12 |
| 6,099,530 A * | 8/2000 | Simonian et al. | 606/75 |
| 6,099,568 A * | 8/2000 | Simonian et al. | 623/13.11 |
| 6,110,207 A * | 8/2000 | Eichhorn et al. | 623/13.14 |
| 6,159,234 A * | 12/2000 | Bonutti et al. | 606/232 |
| 6,193,754 B1 * | 2/2001 | Seedhom | 623/13.11 |
| 6,203,572 B1 * | 3/2001 | Johnson et al. | 623/13.15 |
| 6,283,996 B1 * | 9/2001 | Chervitz et al. | 623/13.14 |
| 6,296,659 B1 * | 10/2001 | Foerster | 606/224 |
| 6,325,804 B1 * | 12/2001 | Wenstrom et al. | 623/13.12 |
| 6,533,802 B2 * | 3/2003 | Bojarski et al. | 606/232 |
| 6,802,862 B1 * | 10/2004 | Roger et al. | 623/13.14 |
| 7,097,654 B1 * | 8/2006 | Freedland | 606/232 |
| 7,494,506 B2 * | 2/2009 | Brulez et al. | 623/13.11 |
| 7,601,165 B2 * | 10/2009 | Stone | 606/232 |
| 7,658,751 B2 * | 2/2010 | Stone et al. | 606/232 |
| 7,686,838 B2 * | 3/2010 | Wolf et al. | 606/325 |
| 7,749,250 B2 * | 7/2010 | Stone et al. | 606/232 |
| 7,776,039 B2 * | 8/2010 | Bernstein et al. | 606/74 |
| 7,819,898 B2 * | 10/2010 | Stone et al. | 606/232 |
| 7,828,855 B2 * | 11/2010 | Ellis et al. | 623/23.74 |
| 7,875,057 B2 * | 1/2011 | Cook et al. | 606/232 |
| 7,905,903 B2 * | 3/2011 | Stone et al. | 606/232 |
| 7,914,539 B2 * | 3/2011 | Stone et al. | 606/104 |
| 8,109,965 B2 * | 2/2012 | Stone et al. | 606/232 |
| 8,118,836 B2 * | 2/2012 | Denham et al. | 606/232 |
| 8,162,997 B2 * | 4/2012 | Struhl | 606/300 |
| 8,206,446 B1 * | 6/2012 | Montgomery | 623/13.14 |
| 8,231,654 B2 * | 7/2012 | Kaiser et al. | 606/232 |
| 2001/0041938 A1 * | 11/2001 | Hein | 623/13.13 |
| 2002/0161439 A1 * | 10/2002 | Strobel et al. | 623/13.14 |
| 2002/0173788 A1 * | 11/2002 | Bojarski et al. | 606/60 |
| 2003/0114929 A1 * | 6/2003 | Knudsen et al. | 623/13.19 |
| 2004/0015171 A1 * | 1/2004 | Bojarski et al. | 606/72 |
| 2004/0059415 A1 * | 3/2004 | Schmieding | 623/13.12 |
| 2004/0073306 A1 * | 4/2004 | Eichhorn et al. | 623/13.11 |
| 2004/0243235 A1 * | 12/2004 | Goh et al. | 623/13.17 |
| 2004/0267360 A1 * | 12/2004 | Huber | 623/13.12 |
| 2005/0004670 A1 * | 1/2005 | Gebhardt et al. | 623/13.14 |
| 2005/0033363 A1 * | 2/2005 | Bojarski et al. | 606/228 |
| 2005/0065533 A1 * | 3/2005 | Magen et al. | 606/102 |
| 2005/0070906 A1 * | 3/2005 | Clark et al. | 606/72 |
| 2005/0137704 A1 * | 6/2005 | Steenlage | 623/13.14 |
| 2005/0149187 A1 * | 7/2005 | Clark et al. | 623/13.12 |
| 2005/0171603 A1 * | 8/2005 | Justin et al. | 623/13.14 |
| 2005/0203623 A1 * | 9/2005 | Steiner et al. | 623/13.14 |
| 2005/0261766 A1 * | 11/2005 | Chervitz et al. | 623/13.14 |
| 2006/0067971 A1 * | 3/2006 | Story et al. | 424/426 |
| 2006/0095130 A1 * | 5/2006 | Caborn et al. | 623/13.14 |
| 2006/0142769 A1 * | 6/2006 | Collette | 606/73 |
| 2006/0265064 A1 * | 11/2006 | Re et al. | 623/13.14 |
| 2007/0021839 A1 * | 1/2007 | Lowe | 623/21.11 |
| 2007/0118217 A1 * | 5/2007 | Brulez et al. | 623/13.2 |
| 2007/0162123 A1 * | 7/2007 | Whittaker et al. | 623/13.14 |
| 2007/0162125 A1 * | 7/2007 | LeBeau et al. | 623/13.14 |
| 2007/0179531 A1 | 8/2007 | Thornes | |
| 2007/0225805 A1 * | 9/2007 | Schmieding | 623/13.14 |
| 2007/0239209 A1 * | 10/2007 | Fallman | 606/232 |
| 2007/0239275 A1 * | 10/2007 | Willobee | 623/13.17 |
| 2007/0250163 A1 * | 10/2007 | Cassani | 623/13.17 |
| 2007/0270857 A1 * | 11/2007 | Lombardo et al. | 606/72 |
| 2008/0046009 A1 | 2/2008 | Albertorio et al. | |
| 2008/0082127 A1 * | 4/2008 | Stone et al. | 606/232 |
| 2008/0188935 A1 * | 8/2008 | Saylor et al. | 623/13.14 |
| 2008/0188936 A1 * | 8/2008 | Ball et al. | 623/13.14 |
| 2008/0215150 A1 * | 9/2008 | Koob et al. | 623/13.14 |
| 2008/0228271 A1 * | 9/2008 | Stone et al. | 623/13.12 |
| 2008/0234819 A1 * | 9/2008 | Schmieding et al. | 623/13.14 |
| 2008/0243248 A1 * | 10/2008 | Stone et al. | 623/13.12 |
| 2008/0275553 A1 * | 11/2008 | Wolf et al. | 623/13.14 |
| 2008/0275554 A1 * | 11/2008 | Iannarone et al. | 623/13.14 |
| 2008/0300683 A1 * | 12/2008 | Altman et al. | 623/13.11 |
| 2008/0312689 A1 * | 12/2008 | Denham et al. | 606/232 |
| 2009/0018654 A1 * | 1/2009 | Schmieding et al. | 623/13.14 |
| 2009/0030516 A1 * | 1/2009 | Imbert | 623/13.14 |
| 2009/0054982 A1 * | 2/2009 | Cimino | 623/13.19 |
| 2009/0062854 A1 * | 3/2009 | Kaiser et al. | 606/232 |
| 2009/0187244 A1 * | 7/2009 | Dross | 623/13.14 |
| 2009/0216326 A1 * | 8/2009 | Hirpara et al. | 623/13.14 |
| 2009/0228017 A1 * | 9/2009 | Collins | 606/96 |
| 2009/0234451 A1 * | 9/2009 | Manderson | 623/13.14 |
| 2009/0265003 A1 * | 10/2009 | Re et al. | 623/13.14 |
| 2009/0306711 A1 * | 12/2009 | Stone et al. | 606/232 |
| 2009/0306776 A1 * | 12/2009 | Murray | 623/13.12 |
| 2009/0306784 A1 * | 12/2009 | Blum | 623/20.21 |
| 2009/0312776 A1 * | 12/2009 | Kaiser et al. | 606/148 |
| 2010/0049258 A1 * | 2/2010 | Dougherty | 606/86 R |
| 2010/0049319 A1 * | 2/2010 | Dougherty | 623/13.11 |
| 2010/0100182 A1 * | 4/2010 | Barnes et al. | 623/13.14 |
| 2010/0145384 A1 * | 6/2010 | Stone et al. | 606/228 |
| 2010/0145448 A1 * | 6/2010 | Montes De Oca Balderas et al. | 623/13.14 |
| 2010/0211075 A1 * | 8/2010 | Stone | 606/70 |
| 2010/0211173 A1 * | 8/2010 | Bardos et al. | 623/13.11 |
| 2010/0249930 A1 * | 9/2010 | Myers | 623/13.14 |
| 2010/0256677 A1 * | 10/2010 | Albertorio et al. | 606/232 |
| 2010/0268273 A1 * | 10/2010 | Albertorio et al. | 606/232 |
| 2010/0268275 A1 * | 10/2010 | Stone et al. | 606/232 |
| 2010/0274355 A1 * | 10/2010 | Mcguire et al. | 623/13.14 |
| 2010/0274356 A1 * | 10/2010 | Fening et al. | 623/13.14 |
| 2010/0292792 A1 * | 11/2010 | Stone et al. | 623/13.14 |
| 2010/0305709 A1 * | 12/2010 | Metzger et al. | 623/20.27 |
| 2010/0312341 A1 * | 12/2010 | Kaiser et al. | 623/13.14 |
| 2010/0318188 A1 * | 12/2010 | Linares | 623/13.14 |
| 2010/0324676 A1 * | 12/2010 | Albertorio et al. | 623/13.14 |
| 2010/0331975 A1 * | 12/2010 | Nissan et al. | 623/4.1 |
| 2011/0040380 A1 * | 2/2011 | Schmieding et al. | 623/13.14 |
| 2011/0046734 A1 * | 2/2011 | Tobis et al. | 623/13.14 |
| 2011/0054609 A1 * | 3/2011 | Cook et al. | 623/13.12 |
| 2011/0087280 A1 * | 4/2011 | Albertorio | 606/232 |
| 2011/0087284 A1 * | 4/2011 | Stone et al. | 606/232 |
| 2011/0098727 A1 * | 4/2011 | Kaiser et al. | 606/144 |
| 2011/0112640 A1 * | 5/2011 | Amis et al. | 623/13.14 |
| 2011/0112641 A1 * | 5/2011 | Justin et al. | 623/13.14 |
| 2011/0118838 A1 * | 5/2011 | Delli-Santi et al. | 623/13.14 |
| 2011/0137416 A1 * | 6/2011 | Myers | 623/13.14 |
| 2011/0184227 A1 * | 7/2011 | Altman et al. | 600/37 |
| 2011/0196432 A1 * | 8/2011 | Griffis, III | 606/86 R |
| 2011/0196490 A1 * | 8/2011 | Gadikota et al. | 623/13.14 |
| 2011/0218625 A1 * | 9/2011 | Berelsman et al. | 623/13.14 |
| 2011/0238179 A1 * | 9/2011 | Laurencin et al. | 623/13.19 |
| 2011/0270278 A1 * | 11/2011 | Overes et al. | 606/144 |
| 2011/0276137 A1 * | 11/2011 | Seedhom et al. | 623/13.11 |
| 2011/0288635 A1 * | 11/2011 | Miller et al. | 623/2.1 |
| 2011/0301707 A1 * | 12/2011 | Buskirk et al. | 623/13.14 |
| 2011/0301708 A1 * | 12/2011 | Stone et al. | 623/13.14 |
| 2012/0046746 A1 * | 2/2012 | Konicek | 623/13.14 |
| 2012/0046747 A1 * | 2/2012 | Justin et al. | 623/13.14 |
| 2012/0053630 A1 * | 3/2012 | Denham et al. | 606/232 |
| 2012/0089143 A1 * | 4/2012 | Martin et al. | 606/62 |
| 2012/0109299 A1 * | 5/2012 | Li et al. | 623/13.14 |
| 2012/0123541 A1 * | 5/2012 | Albertorio et al. | 623/13.14 |
| 2012/0150297 A1 * | 6/2012 | Denham et al. | 623/13.14 |
| 2012/0165938 A1 * | 6/2012 | Denham et al. | 623/13.14 |
| 2012/0197271 A1 * | 8/2012 | Astorino et al. | 606/148 |
| 2012/0296345 A1 * | 11/2012 | Wack et al. | 606/139 |

* cited by examiner

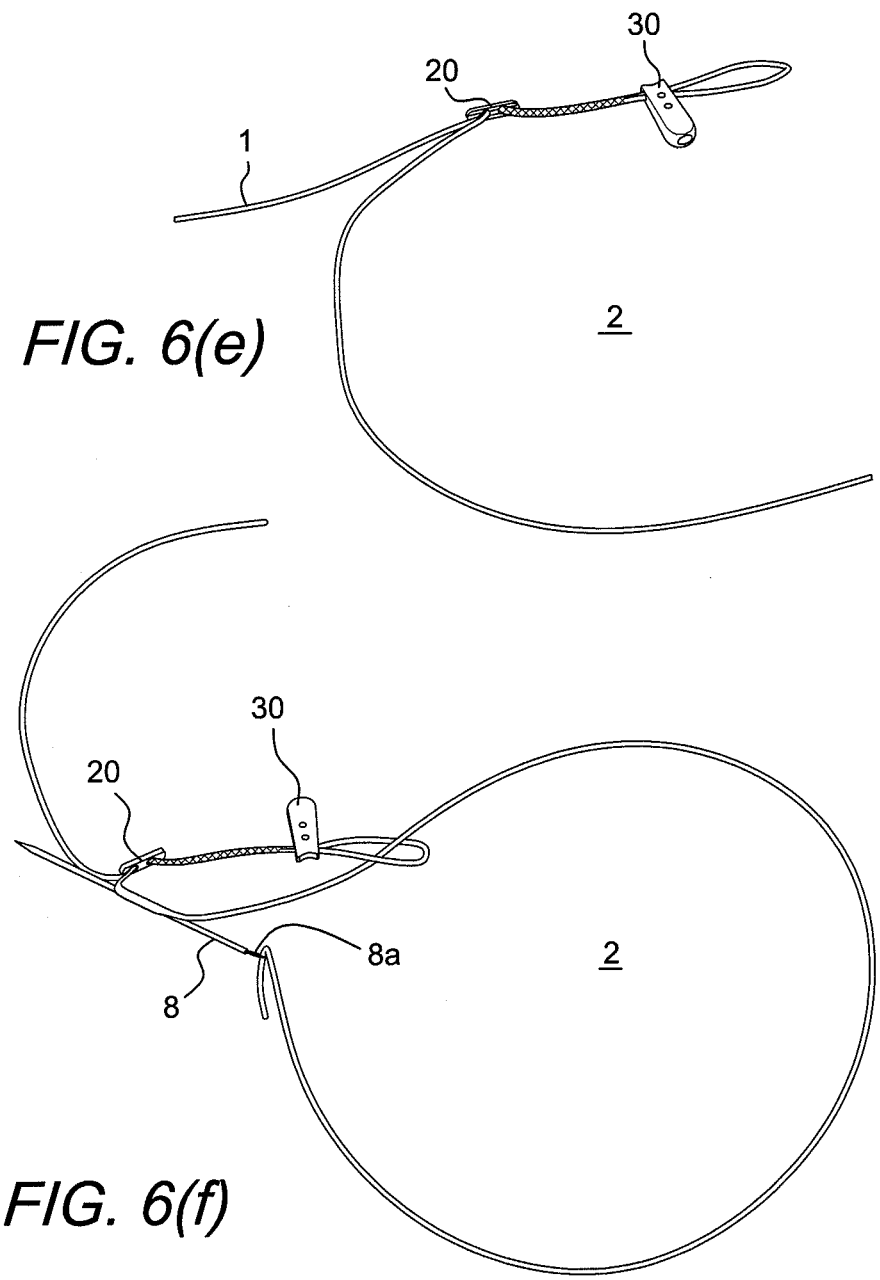
FIG. 6(e)
FIG. 6(f)
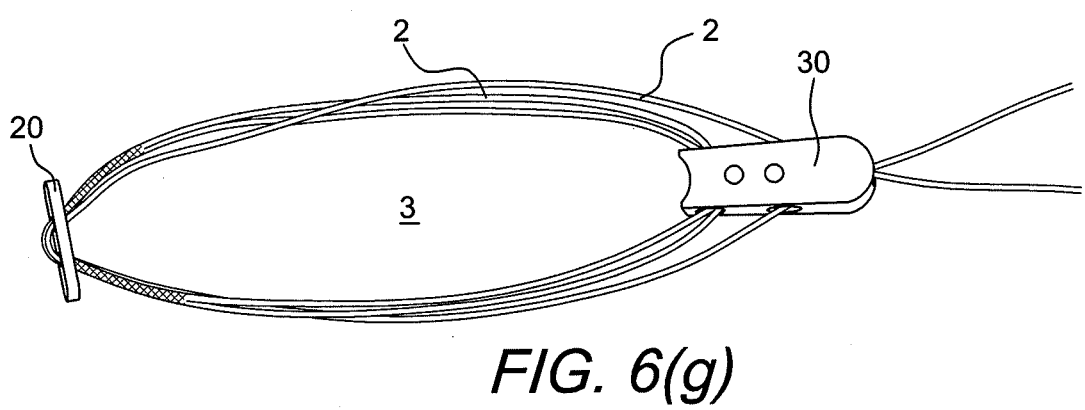
FIG. 6(g)

INTEGRATED ADJUSTABLE BUTTON-SUTURE-GRAFT CONSTRUCT WITH TWO FIXATION DEVICES

CROSS-REFERENCE TO RELATED APPLICATIONS

This application claims the benefit of U.S. Provisional Application No. 61/165,343, filed Mar. 31, 2009, U.S. Provisional Application No. 61/259,507, filed Nov. 9, 2009, U.S. Provisional Patent Application No. 61/311,234, filed Mar. 5, 2010, and U.S. Provisional Patent Application No. 61/311,211, filed Mar. 5, 2010, the entire disclosures of which are incorporated by reference herein.

FIELD OF THE INVENTION

The present invention relates to the field of surgery reconstruction and, more particularly, to joint or ligament reconstruction techniques and associated fixation and reconstruction devices.

BACKGROUND OF THE INVENTION

Reconstructive surgeries, particularly anterior cruciate ligament (ACL) reconstruction, are well-known in the art. Methods of ACL reconstruction using interference screw fixation are described, for example, in U.S. Pat. Nos. 5,211,647 and 5,320,626. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like.

Fixation of the graft (for example, a semitendonosus allograft) within the two knee sockets (i.e., the femoral and tibial tunnels or sockets) requires determination of the proper graft length (soft tissue graft or BTB graft) which in turn is calculated based on the entire length of the sockets plus the intraarticular space between them. Proper determination of the graft length ensures accurate placement of the graft within the femoral and tibial tunnels (sockets).

The devices and methods of ligament reconstruction of the present invention provide an alternative fixation technique that employs at least one button with an adjustable suture loop attached to at least one fixation device (for example, a wedge, an implant, a plug, or an anchor for supporting a graft or a ligament) for improved fixation and exact determination of the graft length within the bone sockets.

SUMMARY OF THE INVENTION

The reconstruction system of the present invention comprises at least one button/loop construct with a flexible, adjustable loop integrated with first and second fixation devices (for example, two wedges, anchors, plugs or implants) that are further attached to tissue (such as soft tissue, graft, tendon, ligament, synthetic material, biological material, bone, or combinations of such materials, among others).

The at least one button/loop construct has an adjustable loop length and allows adjustment in one direction while preventing or locking the construct from loosening in the opposite direction, due to applied tensile forces. Preferably, two button/loop constructs are connected to two fixation devices (for example, two wedges) that are secured to a graft or ligament. The adjustable devices facilitate graft fixation by not requiring calculation of the proper transosseous distance in advance. The adjustable devices also provide for both cortical fixation and socket/tunnel compression of the graft or ligament. The wedges occlude the socket/tunnel to prevent fluid extravasation and minimize micromotion of the graft at the bone orifice/graft interface which may lead to tunnel widening. The graft or implant is tensioned in opposing directions. The graft and the two fixation devices are interconnected. The two fixation devices provide for femoral and tibia fixation and are adjustable.

The present invention also provides an integrated system containing a graft or ligament attached to tibial and femoral devices, each of the tibial and femoral devices being attached to a suture-button member capable of adjusting tension (i.e., a suture-button member with an adjustable length). In the integrated system of the present invention, the femoral device, the graft or ligament, and the tibial device are all integrated, in the operating room, into a single unit (saving time for fixation of the system and creating an overall stronger repair). In additional embodiments, the integrated system contains a graft or ligament attached to tibial and femoral devices, each of the tibial and femoral devices being attached to a suture-button member having a fixed length. The tibial and femoral devices may be wedges, plugs, anchors, screws and/or implants, or combination of these devices, among others. These devices may or may not include drive mechanisms which connect to instrumentation to assist in orientation and/or advancement of the device(s).

The method of the present invention comprises the steps of: (i) forming a tunnel or socket through a first bone and a second bone; (ii) providing a button/graft construct including at least one button joined to one of two fixation devices (for example, a wedge or an implant supporting a graft or a ligament) by a loop of flexible material (which may have an adjustable length); (iii) advancing the button through the bones until it exits one of the first and second bones; and (iv) securing each of the fixation devices (with the graft or ligament attached) within each of the first and second bones by adjusting tension and controlling the length of the loop of flexible material.

These and other features and advantages of the invention will be more apparent from the following detailed description that is provided in connection with the accompanying drawing and illustrated exemplary embodiments of the invention.

BRIEF DESCRIPTION OF THE DRAWINGS

FIGS. 6(a)-(g) illustrate exemplary steps of forming/assembling the button/loop construct with a flexible, adjustable loop (a four-point knotless fixation device and locking mechanism) and with a graft fixation device of FIGS. 4 and 5.

DETAILED DESCRIPTION OF THE PREFERRED EMBODIMENTS

Figure 1:
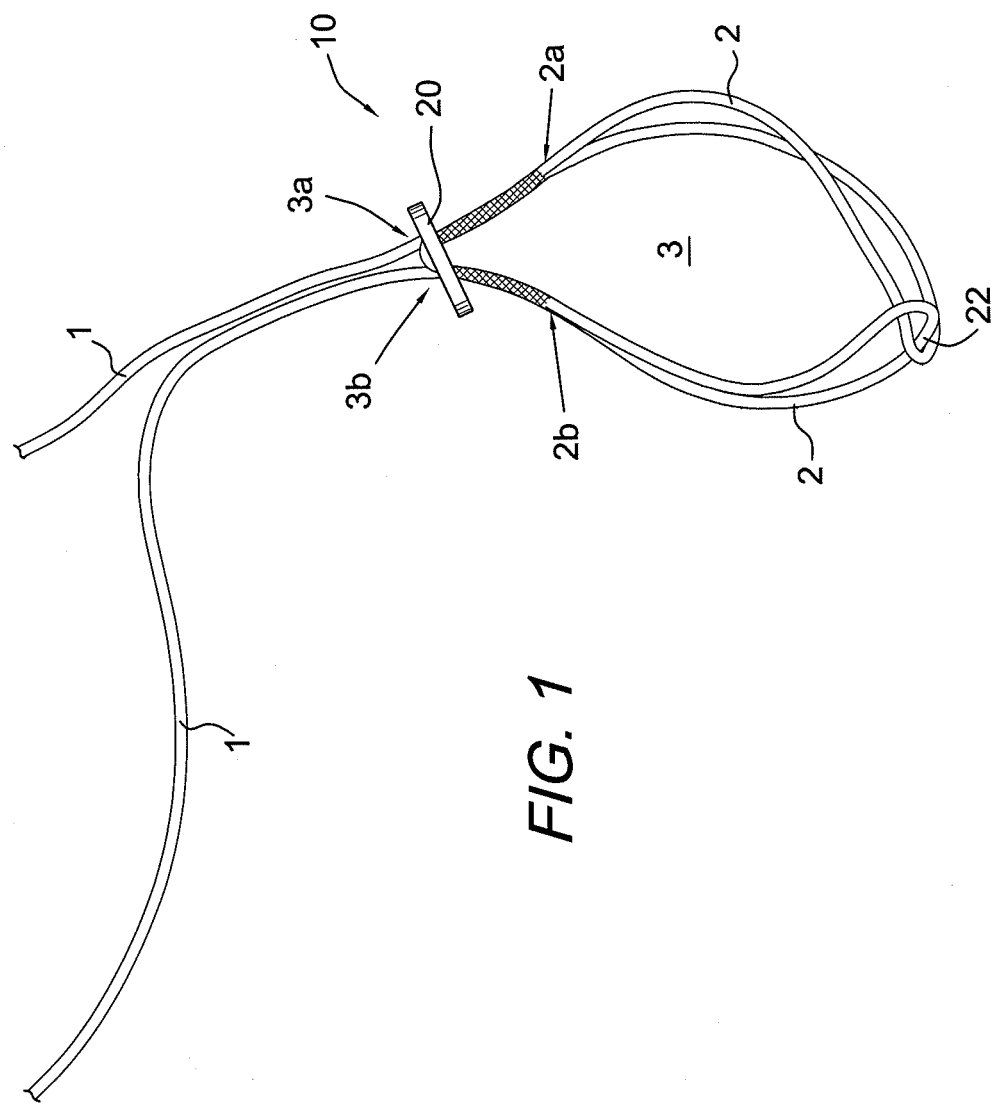
FIGS. 1-3 illustrate various view of a button/loop construct with a flexible, adjustable loop according to the present invention.

The present invention provides a fixation technique that employs at least one button with an adjustable suture loop attached to two fixation devices (for example, wedges, plugs, anchors or implants for supporting a graft) for improved fixation and elimination for the need to calculate the exact transosseous distance for each bone. The graft may be an allograft or an autograft ligament or tendon, or any other biocompatible synthetic material or combination of materials.

The reconstruction system of the present invention preferably comprises a first and second self-locking adjustable constructs (for example, a button with a loop of flexible material) attached to first and second fixation devices (for example, wedges, anchors, plugs, or implants, or a combination of these devices). The flexible material has an adjustable length. The graft or ligament is secured to the fixation devices. The fixation devices may or may not incorporate a drive mechanism for attachment of instrumentation to facilitate orientation or advancement of the device. The adjustable self-locking constructs facilitate graft fixation by not necessitating calculation of the proper graft length in advance. The adjustable self-locking constructs also provide for both cortical fixation and socket/tunnel compression of the graft or ligament. Each of the wedges (the fixation devices) also occludes the socket/tunnel to prevent fluid extravasation and minimizes micromotion of the graft at the bone orifice/graft interface which may lead to tunnel widening.

The present invention also provides an integrated system containing a graft or ligament attached to tibial and femoral devices, each of the tibial and femoral devices being attached to a suture-button member capable of adjusting tension (i.e., a suture-button member with an adjustable length). In additional/alternative embodiments, the integrated system contains a graft or ligament attached to tibial and femoral devices, each of the tibial and femoral device being attached to a suture-button member having a fixed length. The tibial and femoral devices may be wedges, plugs, anchors, screws and/or implants, or combination of these devices, among others.

The method of the present invention comprises the steps of: (i) forming a tunnel or socket through a first bone and a second bone; (ii) providing a button/graft construct including two buttons joined to each of two fixation devices (for example, wedges or implants supporting or securing a graft or a ligament) by a loop of flexible material (which may have an adjustable length); (iii) advancing one button through the bones until it exits the first bone; (iv) securing the first fixation device (with the graft or ligament attached) within the first bone; (v) advancing the other button through the second bone until it exits the second bone to secure the second fixation device within the second bone; and (vi) adjusting the length of at least one of the two loops by pulling on device tensioning suture, to adjust the overall length of the button/graft construct.

Referring now to the drawings, where like elements are designated by like reference numerals, FIGS. 1-13 illustrate various components of final assembly 100 (FIGS. 10-13) of the present invention comprising at least one self-locking adjustable button/loop construct 10 which allows tissue (graft or ligament) 80 to be fully inserted and seated in femoral and tibial tunnels with two fixation devices 30 (such as two wedges, anchors, or plugs, or combination of such fixation devices).

Figure 2:
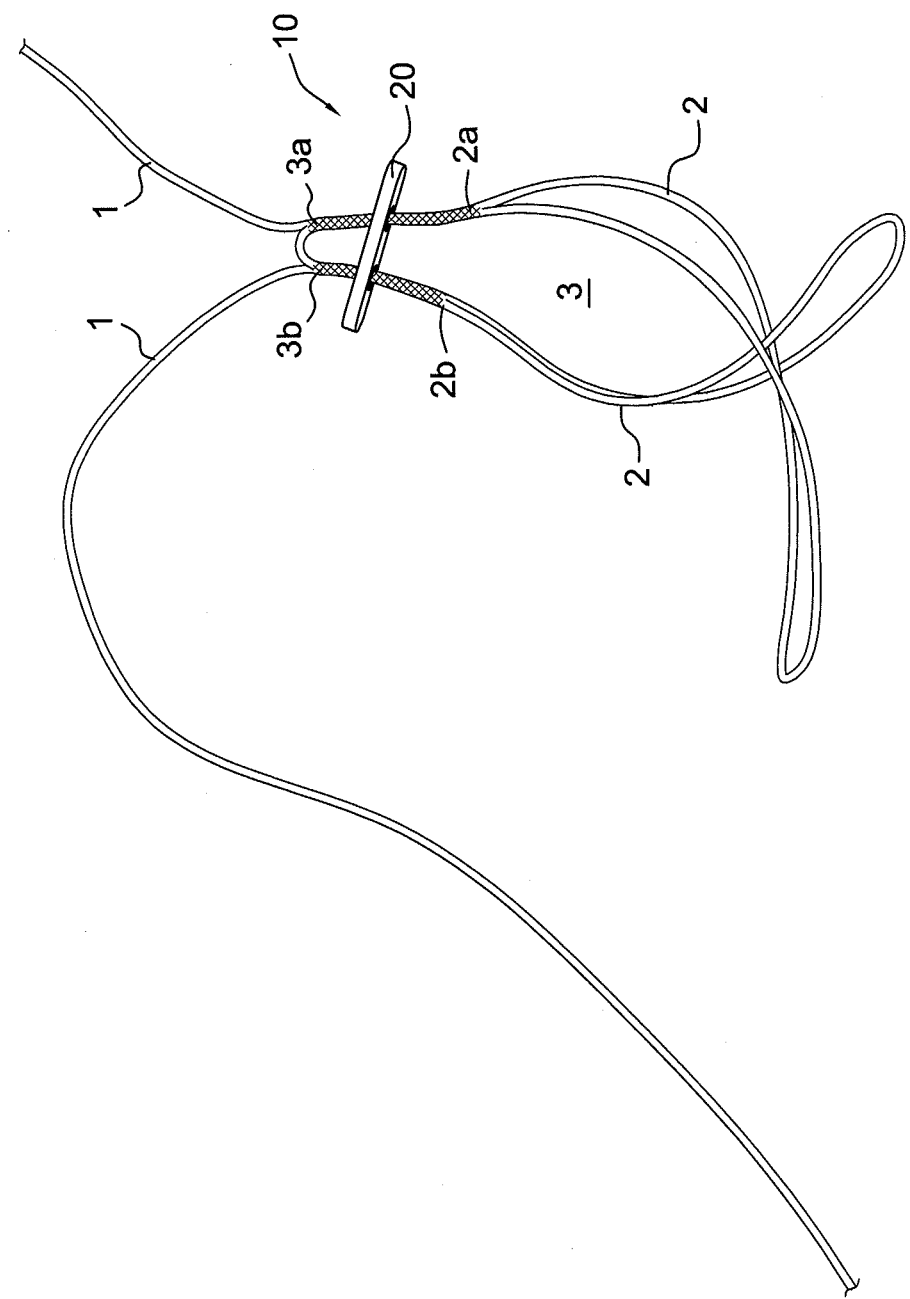
Figure 3:
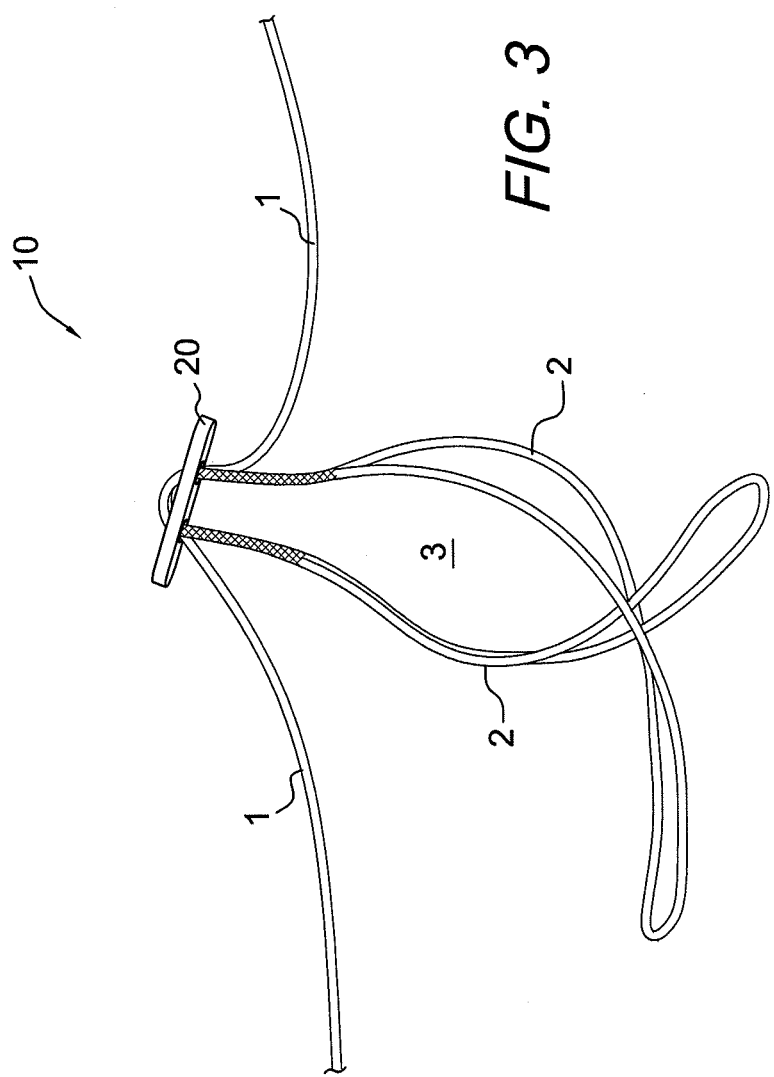

FIGS. 1-3 illustrate a button/loop construct 10 of the present invention comprising a flexible, adjustable loop connected to a fixation device 20 (for example, a button 20). The fixation device provides cortical bone fixation of the graft. The loop has an adjustable length and, as described below, is connected to another fixation device (a wedge) that further supports and secures a graft or ligament. The button/loop construct 10 of the present invention (shown in FIG. 1) is a strong locking mechanism (a four-point knotless locking mechanism) that resists slippage and offers higher than anatomical load failure. As described in more detail below, a graft 80 is secured to wedges 30 and positioned within two bone tunnels using a driver which is received in a socket 36 of wedge 30.

Details regarding the formation/assembly of the self-locking adjustable construct 10 (which allows a graft to be fully inserted and seated in a bone tunnel) are provided in U.S. Provisional Patent Application No. 61/259,507 (filed on Nov. 9, 2009) and U.S. Provisional Patent Application No. 61/311,234 (filed on Mar. 5, 2010), the disclosures of which are incorporated by reference in their entirety herewith.

As described in U.S. Provisional Patent Application Nos. 61/259,507 and 61/311,234, a self-locking adjustable knotless construct (such as construct 10 of FIG. 1) consists of button 20 and flexible material 1 with two adjustable eyesplices (2) that are interconnected to form one adjustable loop (3). By pulling on the free braid strands (1), the individual eyesplices (2) constrict and, in turn, reduce the loop length L (FIG. 4) of loop (3). In order for loop (3) to elongate, a force needs to be applied interior to one or both of the eyesplices (2) to elongate the individual loops.

In a button/loop wedged graft fixation device, and as described in more detail below, the graft is loaded through loop (3) and looped over the wedge 30. By loading the graft through the loop (3) and looped over the wedge 30, the load is placed interior to loop (3) but exterior to the individual eyesplices (2), deflecting the load away from either of the adjustable eyesplices preventing their elongation and, thus, preventing elongation of loop (3).

Exemplary steps of a method of forming/assembling construct 10 of FIGS. 1-3 are detailed in both U.S. Provisional Patent Application Nos. 61/259,507 (filed on Nov. 9, 2009) and 61/311,234 (filed on Mar. 5, 2010), and include as starting materials a suture strand (for example, 50 inches of braided UHMWPE strand); a needle (for example, a blunt tip needle with nitinol loop) and a button (for example, a 3.5 mm titanium button). The suture strand is folded to create two equal length parallel braid strands. At this step, the braid is folded at the midpoint, 25 inches, to create two parallel equal length braid strands (Step 1). At Step 2, a first eyesplice is created on the first strand of braid by passing the blunt tip needle through the center of the braid with the end of the braid being carried through in the nitinol loop of the needle. The splice should travel for a distance of about 17-19 mm through the braid towards the braid midpoint created in Step 1.

Once the first eyesplice has been formed, at Step 3, the button is slid over the non-spliced strand passing the strand through both button holes. The button is slid so that it rests over the first spliced section. At Step 4, a second eyesplice is formed, similar to the first one, with the opposing strand. The strand should be looped through the first eyesplice loop resulting in two eyesplice loops that are interconnected. Again, the splice length should be between 17-19 mm. The splice should be created such that the exiting aperture of the splice is as close as possible to the first eyesplice.

FIG. 1 illustrates free strands 1 of the self-locking adjustable construct 10 pulled back through the button 20 to expose the splice exits points 3a, 3b. Also shown in FIG. 1 are two splice entrance points 2a, 2b. FIG. 2 shows the button 20 adjusted downward to give full view of the two splice entrance points 2a, 2b and the two splice exit points 3a, 3b. FIG. 3 illustrates the final self-locking adjustable construct 10 with no additional splicing occurring and with the free strands 1 passed through the opposite button holes of the button 20.

The button 20 may be formed, for example, of metal, PEEK or PLLA. Details of button 20 are also set forth in U.S. Patent Publ. No. 2007/0179531 (Thornes), the disclosure of which is also incorporated by reference in its entirety herewith. As detailed in U.S. Patent Publ. No. 2007/0179531, the button 20 is provided with at least one opening that allows the passage of the flexible material 1 to pass thereto. The button may be round or oblong and may be provided with two or four apertures.

The flexible material 1 may be suture such as such as a suture braid with braided filaments having a hollow core (for example, strands of suture such as ultrahigh molecular weight polyethylene (UHMWPE) braided with strands of polyester, collagen, or other suture materials, such as PET, PEEK, silk nylon, and absorbable polymers, among many others). The flexible material 1 may also contain a bioabsorbable material, such as PLLA or one of the other polylactides, for example, and/or may be formed of twisted fibers having strands of a contrasting color added to the braided threads, to make the suture more visible during surgical procedures. In exemplary embodiments, flexible material 1 may be a braided suture cover containing strands of a high strength suture material, such as FiberWire® suture, sold by Arthrex, Inc. of Naples, Fla. If desired, the flexible material 1 may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, pliability, handleability or abrasion resistance, for example.

Figure 4:
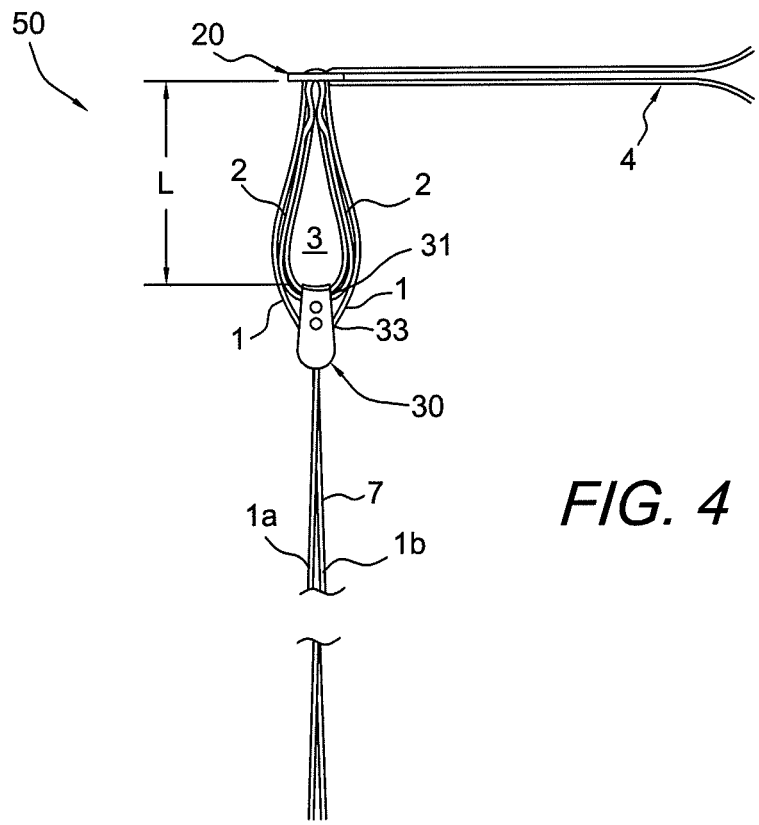
FIG. 4 illustrates a side view of the adjustable button/loop construct of FIGS. 1-3 integrated with a first fixation device (for example, a wedge) according to a first embodiment of the present invention.
Figure 5:
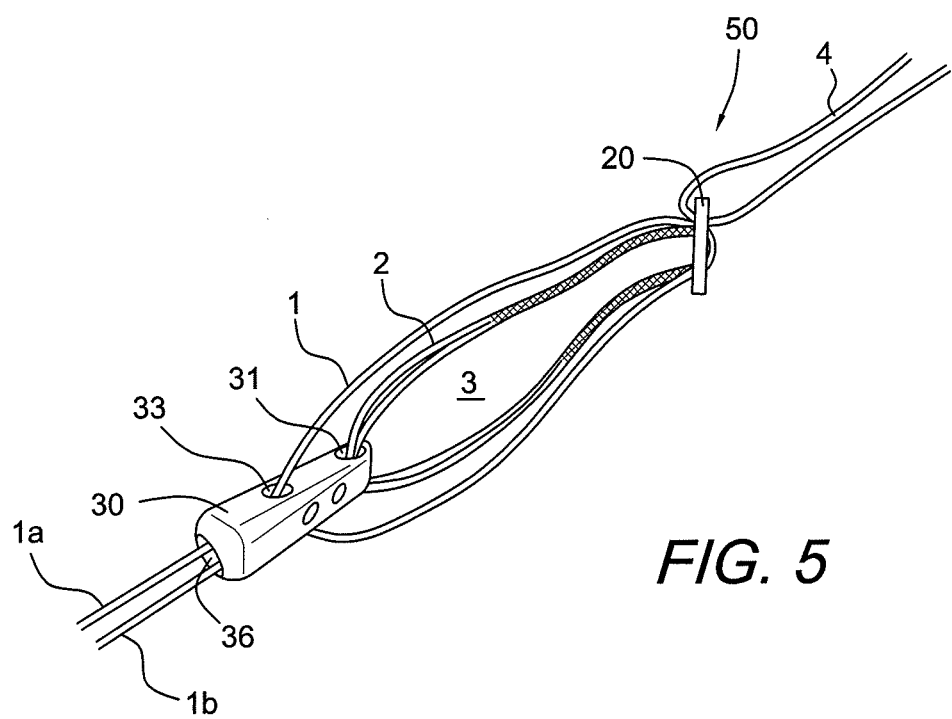
FIG. 5 illustrates a perspective view of the assembly of FIG. 4.
Figure 6:
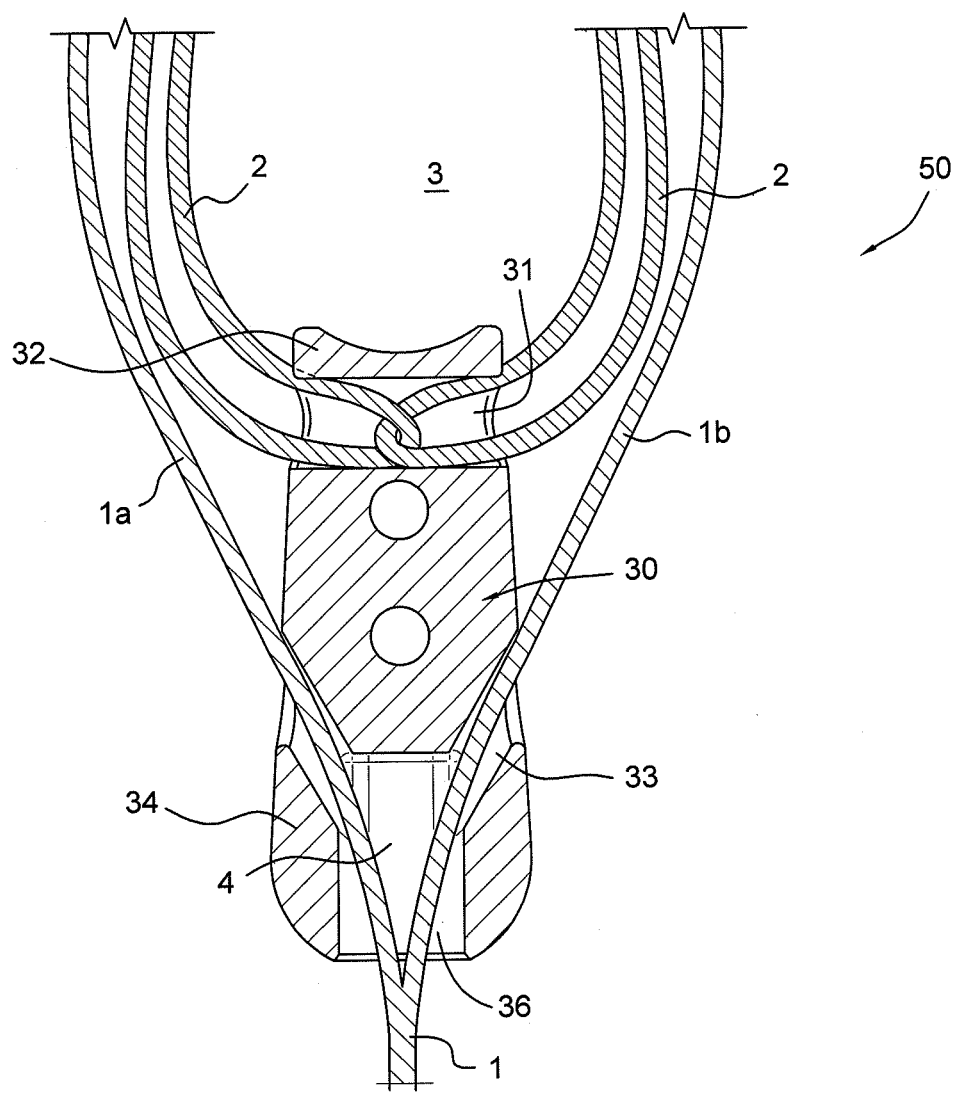
FIG. 6 illustrates a partial, cross-sectional view of the wedge of the assembly of FIG. 5, showing how the suture construct sits in the wedge.

FIGS. 4-6 illustrate the construct of FIG. 1 with a fixation device 30 attached thereto. The fixation device may be a wedge, an anchor, a plug or an implant, among others. If a wedge is employed, the wedge 30 may have a trapezoidal shape (as shown in FIGS. 4-7) or similar shapes, and is provided with a plurality of transversal passages or through holes 31, 33 (FIGS. 4-6) that allow flexible strand 1 of construct 10 to pass therethrough. Socket 36 (FIGS. 5 and 6) is also provided at a most distal end of the wedge 30 to receive a corresponding end of a driver.

Details of a method of attaching the self-locking adjustable construct 10 of FIGS. 1-3 to a fixation device 30 (for example, a wedge 30) to form assembly 50 are set forth in U.S. Provisional Patent Application No. 61/311,211 (filed on Mar. 5, 2010), the disclosure of which is incorporated by reference herewith in its entirety. As detailed in U.S. Provisional Patent Application No. 61/311,211, the eyesplice is passed through the proximal hole 31 of the wedge 30. After the formation of the second eyesplice, the wedge 30 is positioned between the button 20 and eyesplice interconnection 22 (FIG. 1). Once the free end has created the eyesplice, it is passed through both holes of the button and the button is slid to center between the two eyesplice sections. The result is one overall adjustable loop that is comprised of the interconnected adjustable eyesplice loops. For the wedge assembly, the assembly is finished by moving the wedge 30 such that the wedge is positioned over the eyesplice interconnection 33 and the free braid strands 1 are passed through the side holes of the wedge and out of the distal socket 36 (distal hex socket) of wedge 30.

FIGS. 6(a)-(g) illustrate exemplary steps (Steps 1-7) of forming/assembling assembly 50 having the button/loop construct with a flexible, adjustable loop (a four-point knotless fixation device and locking mechanism) and the graft fixation device 30 (also graft supporting device 30).

Figure 6A:
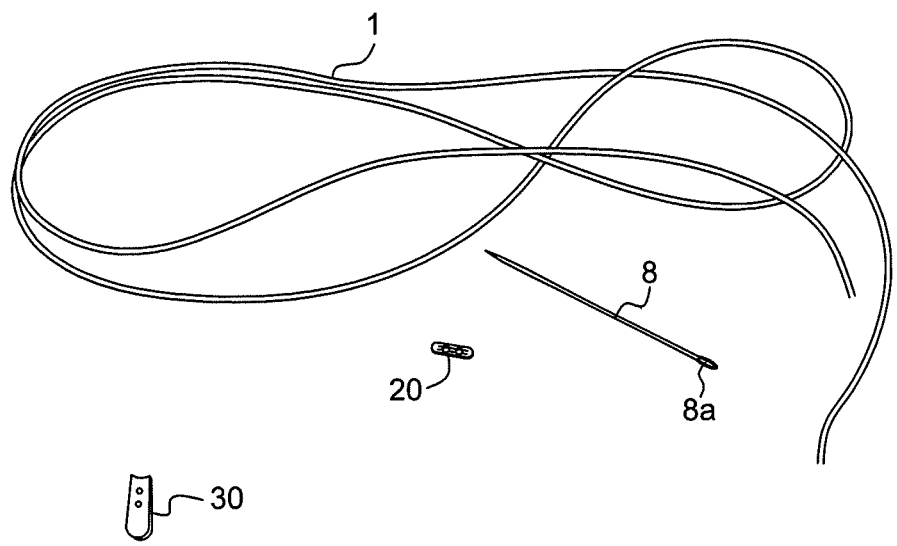

FIG. 6(a) illustrates starting materials: suture strand 1 (for example, 50 inches of braided UHMWPE strand); a suture passing device such as a needle 8 (for example, a blunt tip needle with nitinol loop 8a); a button 20 (for example, a 3.5 mm titanium button); and a wedge 30 (for example, a PEEK femoral wedge for wedge assemblies).

Figure 6B:
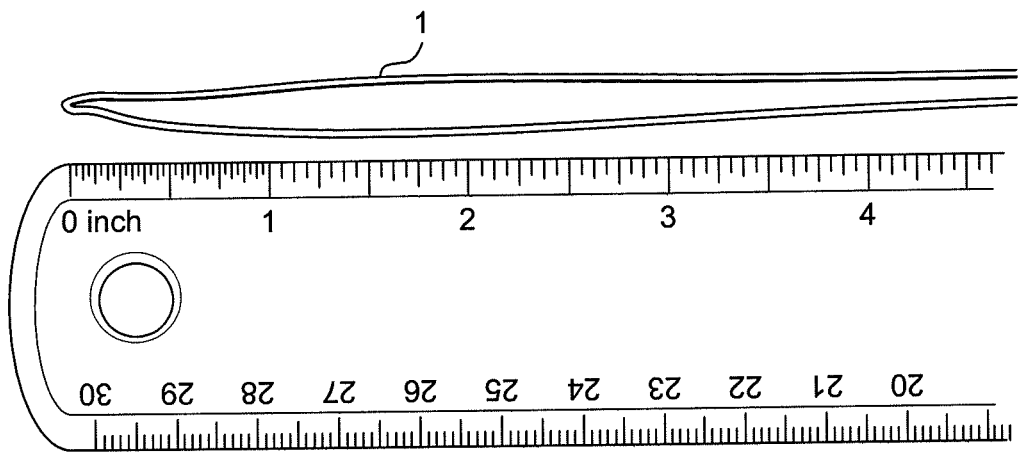

FIG. 6(b) illustrates the suture strand 1 folded to create two equal length parallel braid strands. At this step, the braid 1 is folded at the midpoint, 25 inches, to create two parallel equal length braid strands (Step 1).

Figure 6C:
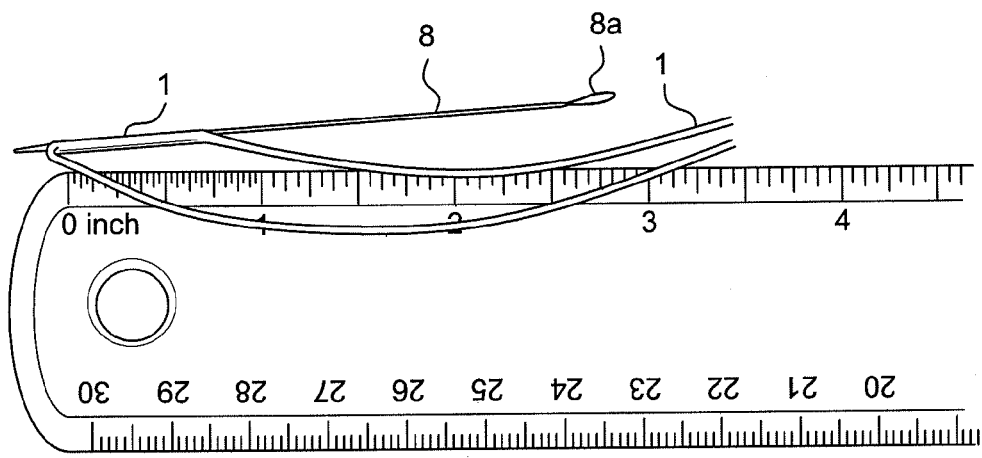

FIG. 6(c) shows the measurement of the eyesplice. At this step (Step 2), an eyesplice 2 is created on the first strand of braid 1 by passing the blunt tip needle 8 through the center of the braid 1 with the end of the braid being carried through in the nitinol loop 8a of the needle 8. The splice should travel for a distance of about 17-19 mm through the braid towards the braid midpoint created in Step 1.

Figure 6D:
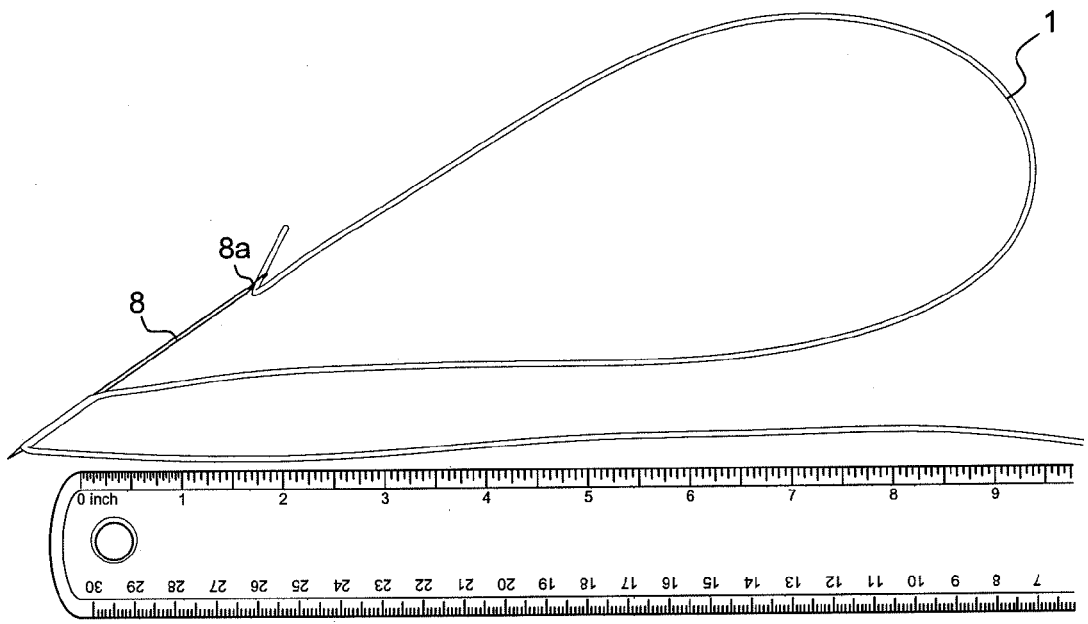

FIG. 6(d) shows the braid carried though the splice 1 with the nitinol loop 8a of needle 8.

FIG. 6(e) shows the formation of the first eyesplice 2. Step 3: the button 20 is slid over the non-spliced strand passing the strand through both button holes. Also pass the free strand that results from the eyesplice through the button holes. Slide the button so that it rests over the first spliced section. For the wedge assembly, additionally, pass the eyesplice through the proximal hole of the wedge.

FIG. 6(f) shows the formation of the second eyesplice 2. Step 4: create another eyesplice 2 similar to the first one, with the opposing strand. The strand should be looped through the first eyesplice loop resulting in two eyesplice loops that are interconnected. Again, the splice length should be between 17-19 mm. The splice should be created such that the exiting aperture of the splice is as close as possible to the first eyesplice. On wedge assembling, the wedge 30 should be positioned between the button 20 and eyesplice interconnection as shown in FIG. 6(f).

FIG. 6(g) shows the final braid construct assembly 50. Step 5: once the free end has created the eyesplice, pass it through both holes of the button 20 and slide the button to center between the two eyesplice sections 2. The result is one overall adjustable loop 3 that is comprised of the interconnected adjustable eyesplice loops 2. For the wedge assembly, finish the assembly by moving the wedge 30 such that is positioned over the eyesplice interconnection 22 and pass the free braid strands through the side holes of the wedge and out of the distal hex.

Step 6: After the loop is constructed, the loop may be stretched for approximately 30 seconds at 50 LBF. The force to stretch the loop is preferably applied such that it acts on the overall loop created between the two eyesplices rather than either individual eyesplice loop.

Step 7: Place passing suture through button hole and pull until strands are equal length.

Figure 7:
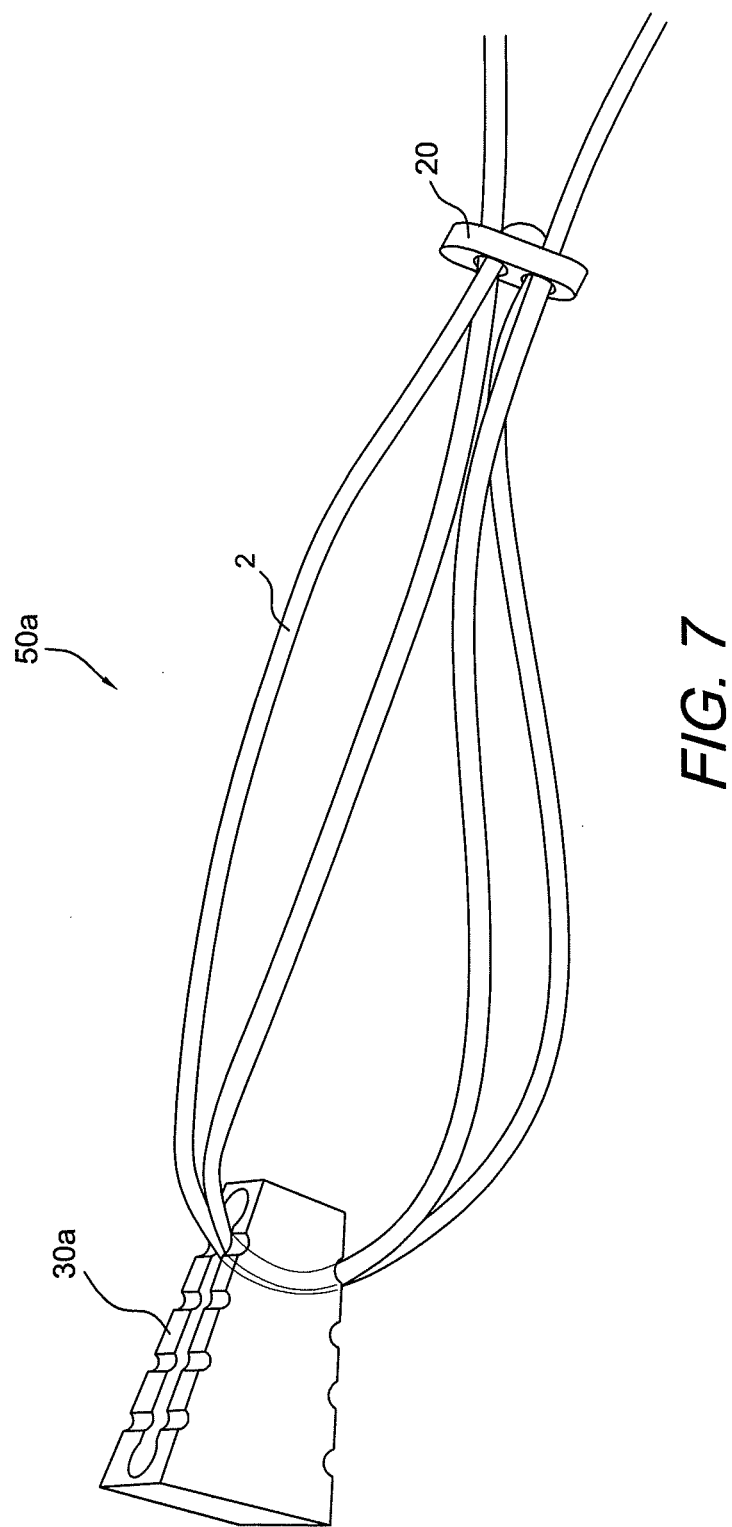
FIG. 7 illustrates a perspective view of the adjustable button/loop construct of FIGS. 1-3 integrated with another fixation device (for example, a trapezoidal wedge) according to a second embodiment of the present invention.
Figure 8:
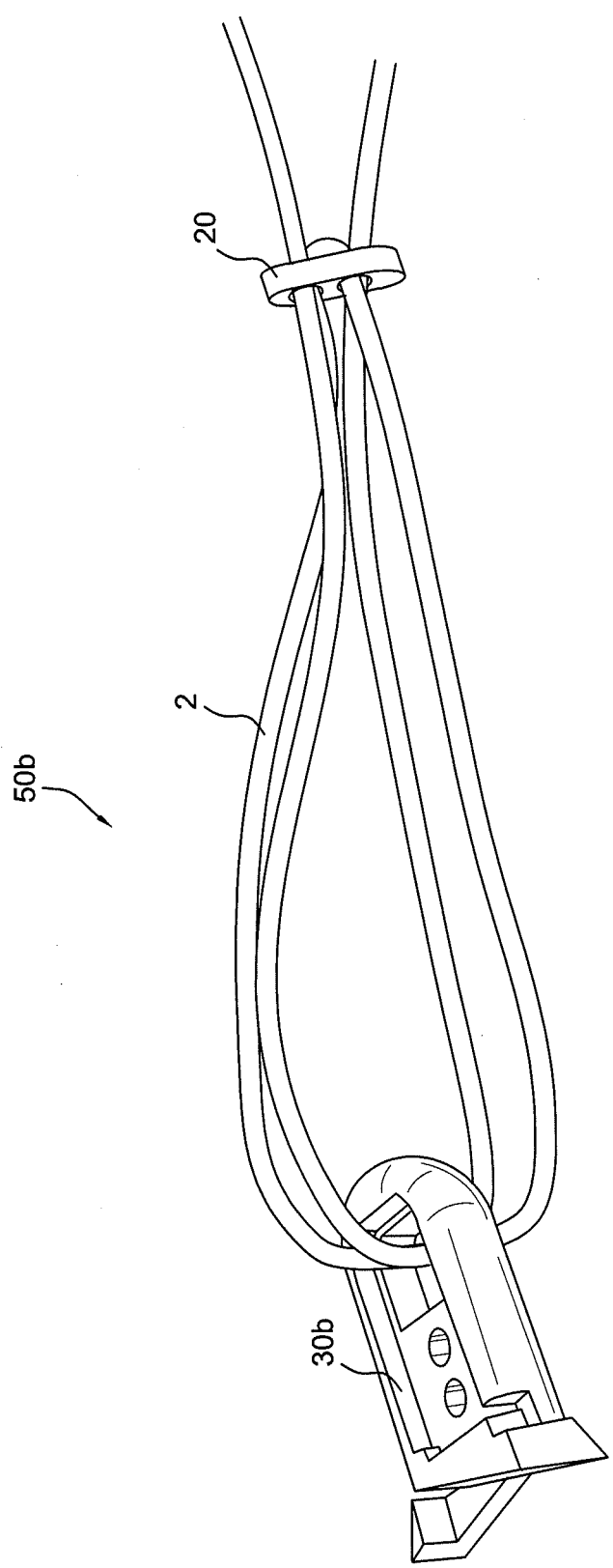
FIG. 8 illustrates a perspective view of the adjustable button/loop construct of FIGS. 1-3 integrated with another fixation device (for example, an expanding plug) according to a third embodiment of the present invention.
Figure 9:
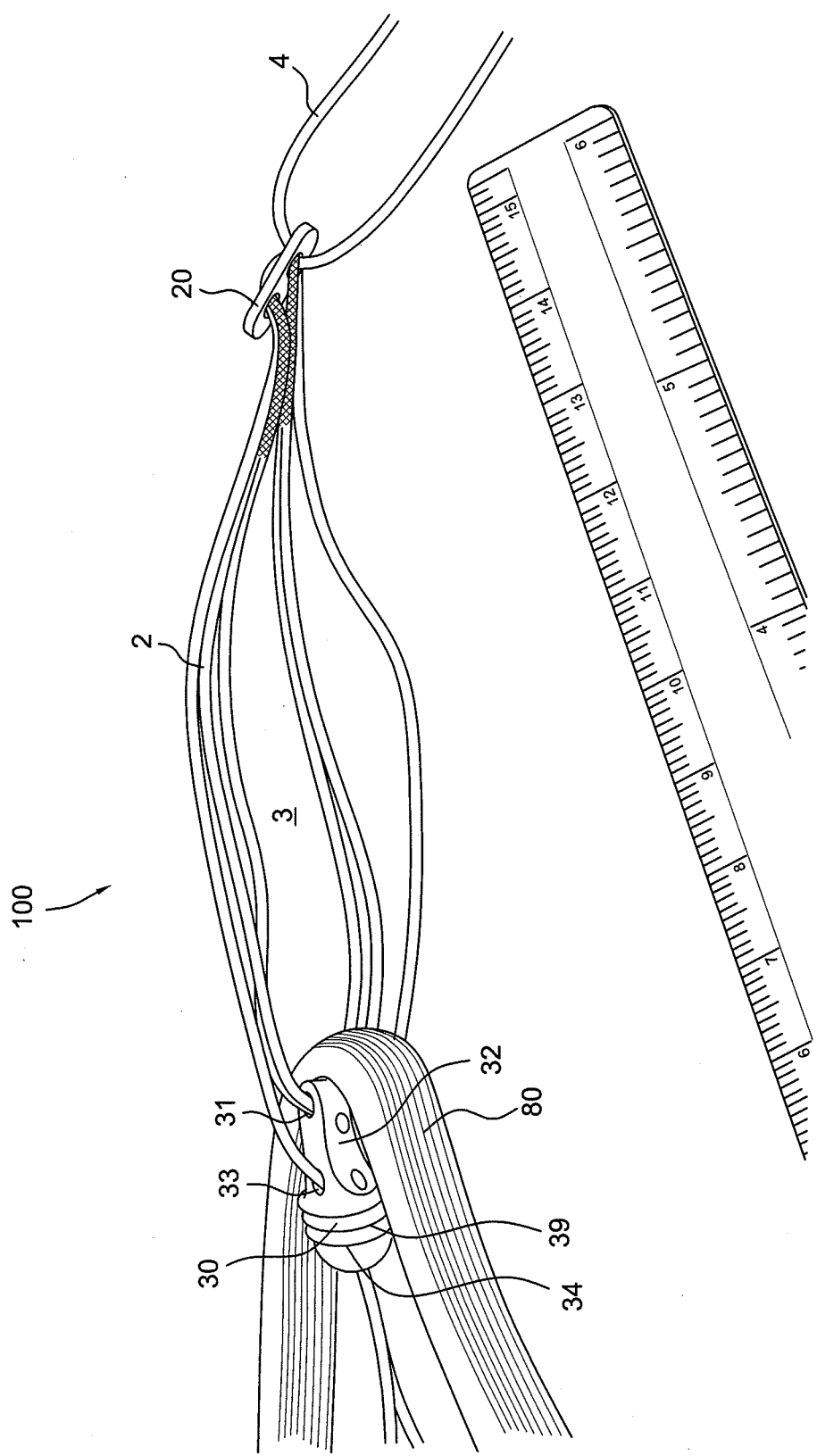
FIG. 9 illustrates the assembly of FIG. 4 (including an adjustable button/loop construct with a wedge) and further provided with a graft or ligament looped over the wedge.
Figure 10:
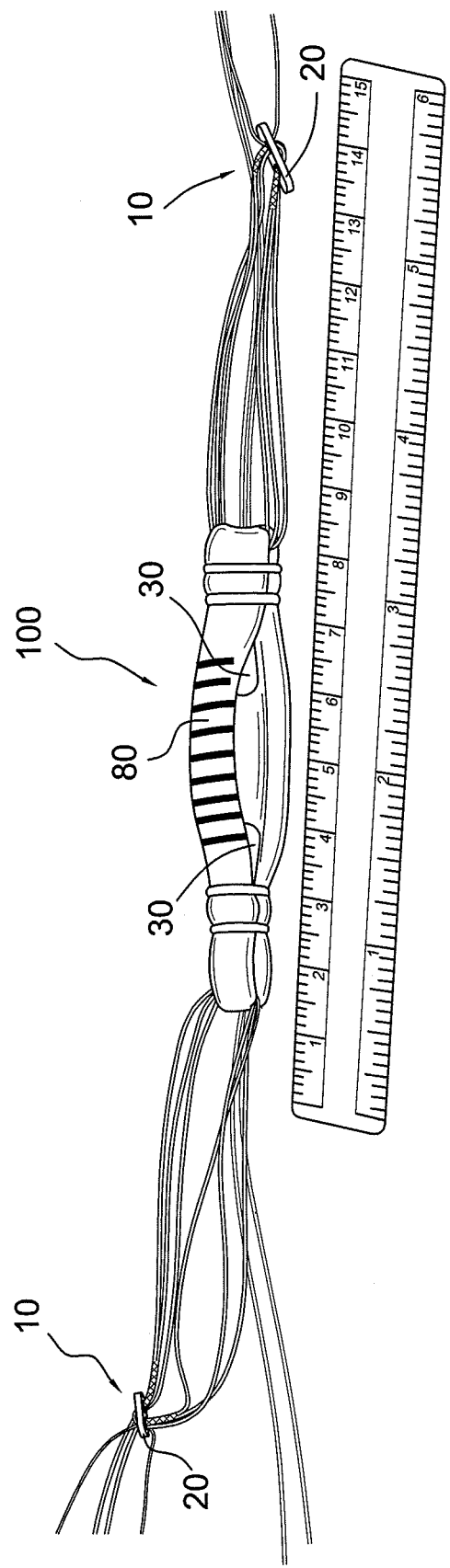
FIG. 10 illustrates a top view of a final assembly of the present invention, including two adjustable button/loop constructs with two attached fixation devices (for example, two wedges) for securing a graft, tendon or ligament.
Figure 11:
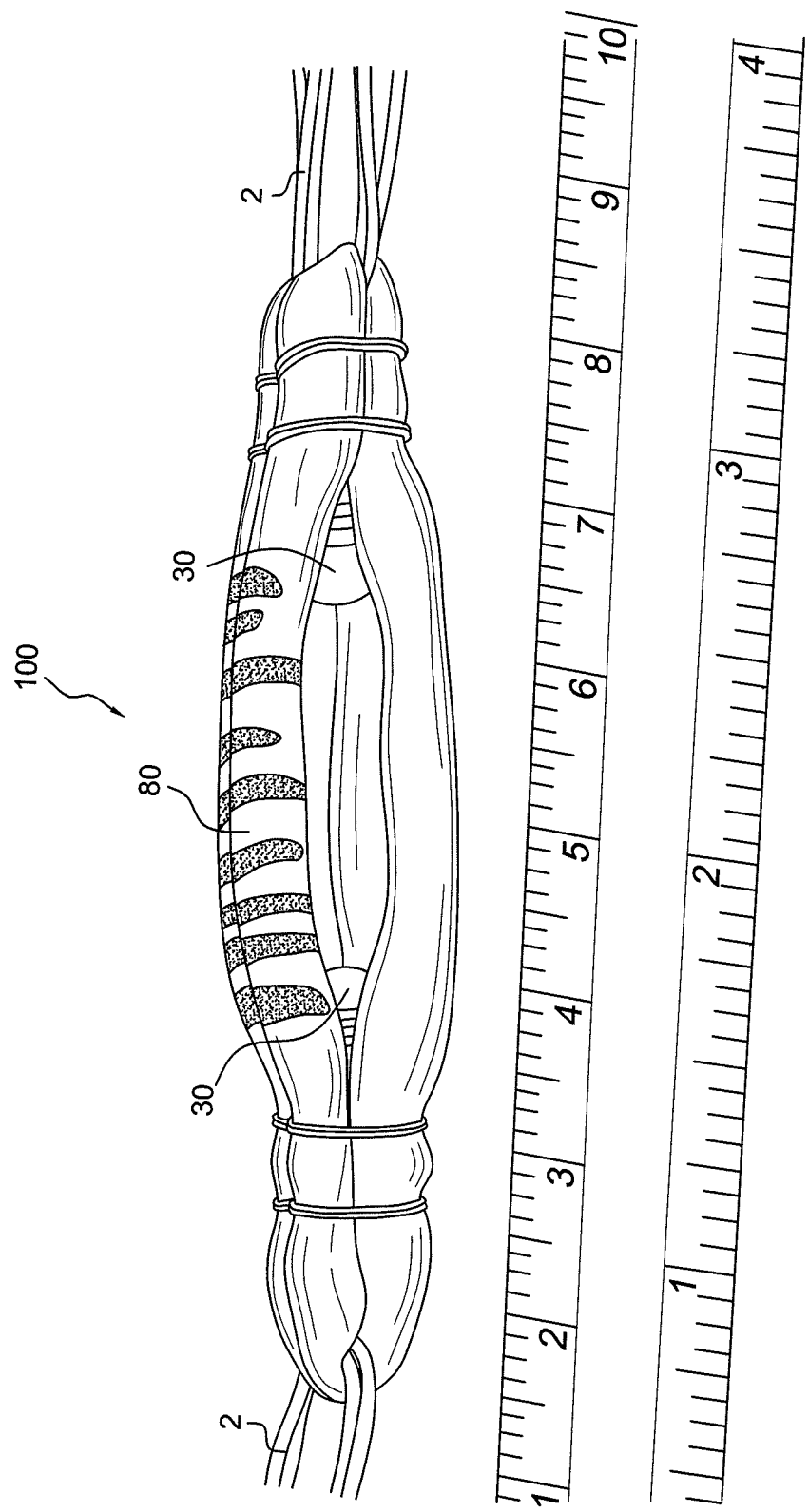
FIG. 11 is an enlarged view of the assembly of FIG. 10.

FIGS. 7 and 8 illustrate assemblies 50a, 50b including the self-locking adjustable construct 10 of FIGS. 1-3 attached to other fixation devices such as fixation device 30a (FIG. 7) or plug 30b (FIG. 8) which are similar to fixation device 30. As detailed below, fixation devices 30, 30a, 30b are employed for preparing and securing soft tissue, graft or ligament within bone tunnels, according to embodiments of the present invention. Plug 30b may be an expanding plug, the details of which are set forth in U.S. Patent Publ. No. 2008/0275554, the disclosure of which is incorporated by reference in its entirety herewith.

FIGS. 9-12 illustrate views of final assembly 100 of the present invention including two self-locking adjustable constructs 10 (FIGS. 1-3) attached to two fixation devices 30 that support and secure tissue (such as soft tissue, graft, tendon, ligament, synthetic material, biological material, bone, or combinations of such materials, among others) 80. FIG. 13 illustrates final assembly 100 of the present invention positioned within the femoral and tibial sockets/tunnels and according to a method of ACL reconstruction of the present invention.

FIGS. 9-12 illustrate assembly 100 (button/wedge/adjustable loop assembly 100) comprising first and second self-locking adjustable knotless constructs 10 (formed of button 20 and two adjustable eyesplices (2) that are interconnected to form one adjustable loop (3)) and two fixation devices 30 (for example, a femoral wedge 30 and a tibial wedge 30, the femoral and tibial wedges being similar or different from each other) with tissue (ligament or graft) 80 attached thereto. The flexible loop of each self-locking adjustable knotless construct 10 is connected to one of the first and second fixation devices 30.

The graft 80 is placed through the open loops of the self-locking adjustable knotless constructs 10 and rest (and are securely positioned) over the wedge "saddle" 30. The soft tissue (graft or ligament) 80 is sutured to each of the fixation devices 30 to prevent the graft from slipping off of the wedge. For example, a whipstitch construct 83 formed by suturing the graft 80 to the fixation devices 30 with fiberloop or free suture is illustrated as part of assembly 100 in FIG. 12.

Figure 12:
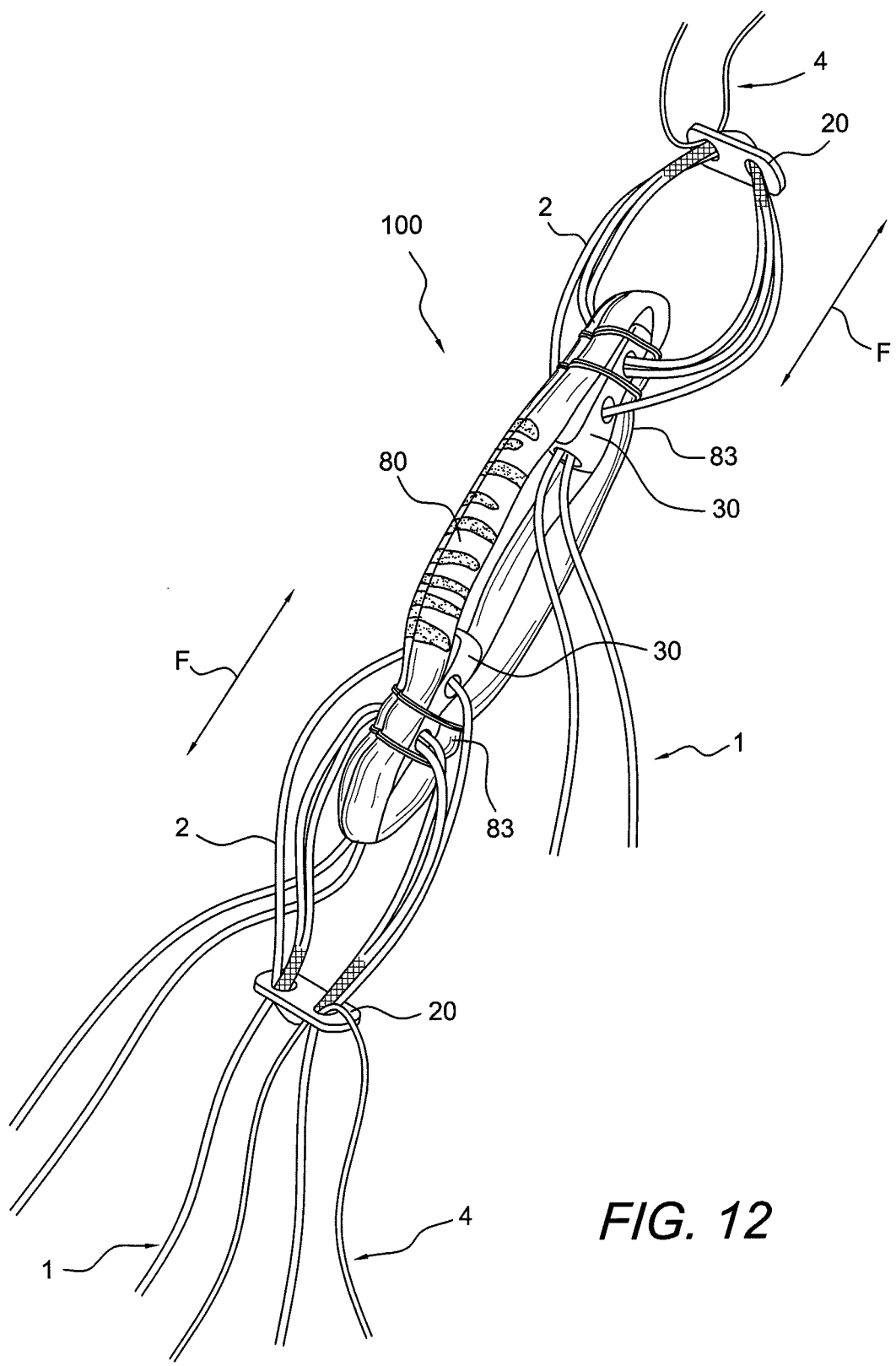
FIG. 12 is another schematic view of the assembly of FIG. 10.
Figure 13:
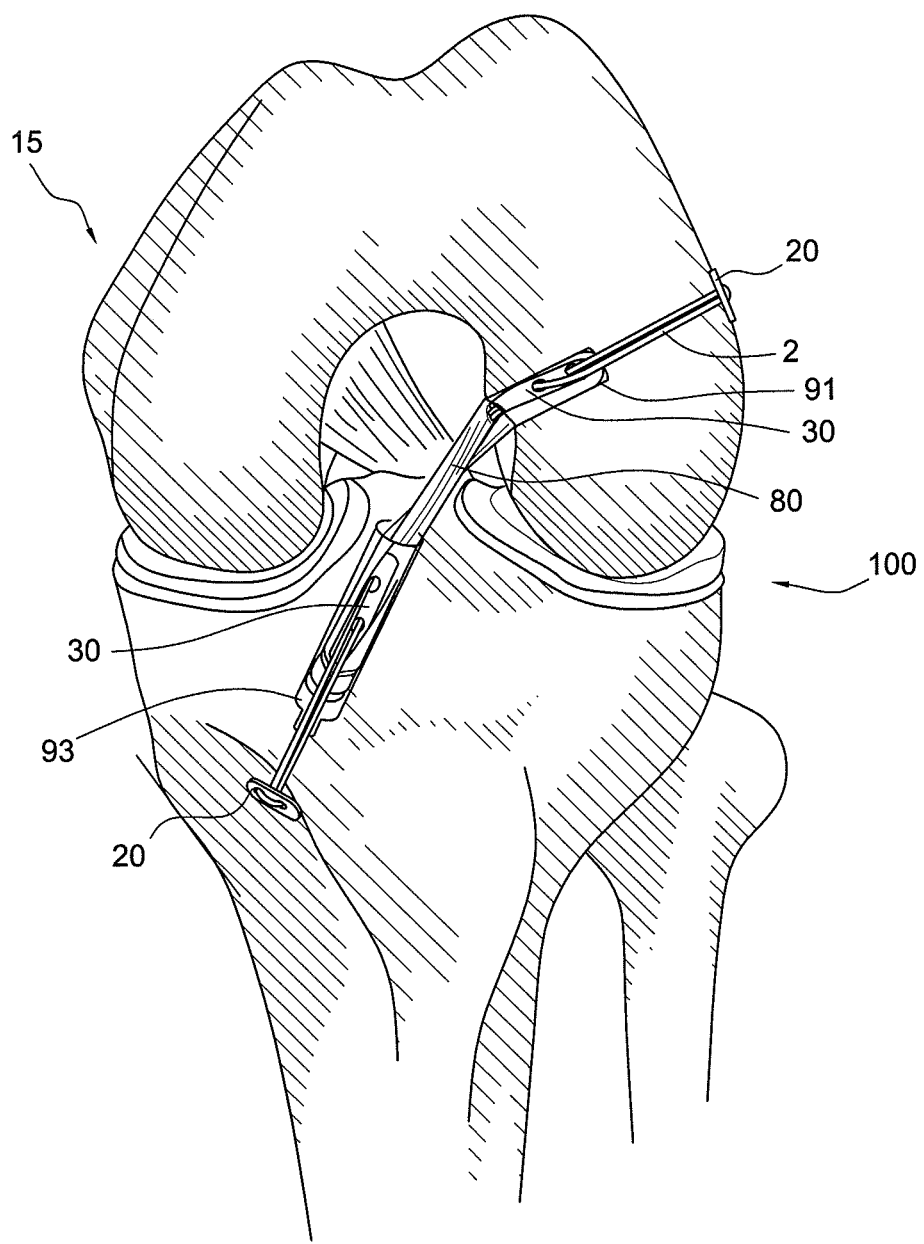
FIG. 13 illustrates the assembly of FIG. 10 positioned within the femoral and tibia sockets/tunnels and according to a method of the present invention.

FIG. 12 illustrates another schematic view of the final assembly 100 of the present invention, detailing button passing sutures 4 and device tensioning sutures 1 already attached to the assembly 100 to aid a surgeon in conducting graft fixation. Graft fixation assembly 100 of the present invention is an integrated system comprising a femoral device 30, graft or ligament 80, and a tibial device 30, all integrated into a single unit 100 (saving time for fixation of the system). The assembly provides cortical fixation on both femur and tibia with buttons. Each of the loops of each of the self-locking adjustable knotless constructs 10 is adjustable under tension (as shown by arrows F1, F2 of FIG. 12). The surgeon simply pulls on both ends of the final construct 100 to adjust the length L of each flexible loop and to tighten, therefore, the construct. In this manner, there is no need for the surgeon to calculate in advance the proper graft length (i.e., the length of the soft tissue graft or of a BTB graft) which in turn is based on calculating the entire length of the tunnels/sockets (i.e., the entire lengths of the femoral and tibial tunnels/sockets) plus the intraarticular space between them.

FIG. 13 shows the final assembly 100 of the present invention being introduced and secured into both a femoral tunnel/socket 91 and a tibial tunnel/socket 93 of knee 15 (typically through an arthroscopic portal). The buttons 20 are pulled out of the bone cortex with the passing sutures (which are later discarded) and self-flip onto the cortex immediately upon exiting. The length of the flexible material 1 is adjusted by being shortened by applying tension to the strands exiting the wedge 30 distally. The distal strands of the flexible material 1 may be further tensioned utilizing an instrument such as a suture tensioner. Each of the wedge 30 (the fixation device) occludes the socket/tunnel 91, 93 (the femoral and tibial tunnel/socket 91, 93) to prevent fluid extravasation. As noted above, the surgeon simply pulls on both ends of the assembly 100 to adjust the length L of each flexible loop of construct 10 and to tighten, therefore, the assembly 100. In this manner, there is no need for the surgeon to calculate in advance the proper graft length and the total length of the femoral and tibia tunnels/sockets and of the intraarticular space between the femoral and tibia tunnels/sockets.

In the integrated system, the femoral device 30, the graft or ligament 80, and the tibial device 30 are all integrated, in the operating room, into a single unit (saving time for fixation of the system and creating an overall stronger repair). In alternative embodiments, the integrated system contains a graft or ligament attached to tibial and femoral devices 30, each of the tibial and femoral devices 30 being attached to a suture-button member 10 having a fixed length. The tibial and femoral devices 30 may be wedges, plugs, anchors, screws and/or implants, or combination of these devices, among others (these devices may be similar to each other, or different from each other). These devices 30 may or may not include drive mechanisms which connect to instrumentation to assist in orientation and/or advancement of the device(s).

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

The invention claimed is:

1. A method of tissue reconstruction, comprising:
providing a first construct attached to a first fixation device, and a second construct attached to a second fixation device, wherein at least one of the first and second constructs is adjustable and is formed of two splices and two adjustable loops that are interconnected;
securing a biological material to the first and second fixation devices to form a biologic construct;
inserting the biologic construct comprising biologic material secured to each of the first and second fixation devices within a first bone tunnel and a second bone tunnel;
securing the first fixation device within the first tunnel and the second fixation device within the second tunnel; and
pulling on the at least one of the first and second constructs that is adjustable to adjust the length of at least one of the first and second constructs without tying knots, to fixate the biologic construct within the first and second bone tunnels.

2. The method of claim 1, wherein both of the first and second constructs have an adjustable length, to allow positioning of the biologic construct within the first and second bone tunnels.

3. The method of claim 1, further comprising the steps of:
   attaching the first construct to a first member with a first configuration and provided with a plurality of first apertures;
   attaching the second construct to a second member with a second configuration and provided with a plurality of second apertures;
   advancing the first member through the first bone tunnel so as to exit the first bone and to pivot and engage a cortical surface of the first bone; and
   advancing the second member through the second bone tunnel so as to exit the second bone and to pivot and engage a cortical surface of the second bone.

4. The method of claim 3, wherein the first member is a button provided with apertures, and the second member is a button provided with apertures, and wherein the first construct is passed through the apertures of the first member and the second construct is passed through the apertures of the second member.

\* \* \* \* \*